United States Patent [19]

Yanagisawa et al.

[11] Patent Number: 5,113,004
[45] Date of Patent: May 12, 1992

[54] ORGANOSILICON COMPOUNDS

[75] Inventors: Hideyoshi Yanagisawa, Gunma; Masaaki Yamaya, Annaka, both of Japan

[73] Assignee: Shin-Etsu Chemical Company, Limited, Tokyo, Japan

[21] Appl. No.: 716,449

[22] Filed: Jun. 17, 1991

[30] Foreign Application Priority Data

Jun. 18, 1990 [JP] Japan ............... 1-160487

[51] Int. Cl.$^5$ .............................. C07F 7/08
[52] U.S. Cl. .................... 556/440; 556/437; 556/41
[58] Field of Search ............ 556/440, 437; 528/10, 528/41

[56] References Cited

U.S. PATENT DOCUMENTS

| | | | |
|---|---|---|---|
| 4,645,844 | 2/1989 | Berger et al. | 556/436 X |
| 4,956,484 | 9/1990 | Gementi et al. | 556/436 X |
| 4,981,986 | 1/1991 | Yoshioka et al. | 556/440 X |
| 5,041,587 | 8/1991 | Itoh et al. | 556/440 X |

Primary Examiner—Arthur C. Prescott
Attorney, Agent, or Firm—Millen, White & Zelano

[57] ABSTRACT

Organosilicon compounds represented by the following general formula, which acquire high thermal resistance suitable for silane coupling agents by containing a phenylene group between an alkoxysilyl group and a (metha)acrylic group;

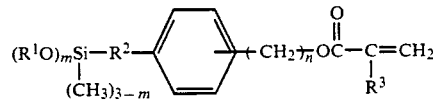

(wherein $R^1$ represents a monovalent hydrocarbon residue containing one or two carbon atoms, $R^2$ represents a divalent hydrocarbon residue containing two or three carbon atoms, $R^3$ represents a hydrogen atom or a methyl group, m represents an integer from 1 to 3, and n represents 0 to 1).

9 Claims, 2 Drawing Sheets

ORGANOSILICON COMPOUNDS

FIELD OF THE INVENTION

This invention relates to organosilicon compounds and, more particularly, to novel organosilicon compounds suitable for a silane coupling agent.

BACKGROUND OF THE INVENTION

A primer treatment of adherents using as an adhesion primer a less viscous solution containing solids, such as reactive low or high molecular compounds, etc., in a relatively low concentration is one of the practical surface treatments for effecting an improvement upon adhesiveness. As examples of such a primer, silane coupling agents are well known. The following three basic functions are to be expected of the foregoing primer treatment; (1) a function of enhancing the affinity of adhesives for the surface of an adherent, (2) a function of reinforcing the surface of an adherent, and (3) a function of protecting the once formed adhesion interface to heighten the durability of adhesiveness. From the standpoint of the effectiveness for those functions, especially for (2) and (3), organosilane compounds containing a (metha) acrylic group have recently enjoyed as silane coupling agent with considerable popularity. In particular, (metha)acryloxyalkylalkoxysilanes, especially γ-methacryloxypropyltrimethoxysilane, are superior in respect that they can not only be used as adhesives between various resins and all kinds of inorganic materials but also make various kinds of resins moisture curable by being grafted on said resins. However, the silane coupling agents of the above-cited kind have a defect that they cannot give satisfaction in thermal resistance.

SUMMARY OF THE INVENTION

As a result of concentrating our energies upon obviation of the above-described defect, it has now been found that thermal resistance of the silane coupling agents of the foregoing type can be heightened by combining an alkoxysilyl group with a (metha)acrylic group via phenyl group, compared with that of conventional methacrylic functional silane compounds, thus achieving this invention.

Therefore, an object of this invention is to provide silae coupling agents excellent in thermal resistance.

The above-described object is attained with organosilicon compounds represented by the following general formula;

wherein $R^1$ represents a monovalent hydrocarbon residue containing one or two carbon atoms, $R^2$ represents a divalent hydrocarbon residue containing two or three carbon atoms, $R^3$ represents a hydrogen atom or a methyl group, m represents an integer from 1 to 3, and n represents 0 or 1.

When the organosilicon compounds of this invention are applied to a silane coupling agent, they can exhibit higher thermal resistance than conventional acrylic functional silane coupling agents, because they contain phenyl group between an alkoxysilyl group and a (metha) acrylic group.

DETAILED DESCRIPTION OF THE INVENTION

In the general formula

$R^1$ represents a monovalent hydrocarbon residue with 1-2 carbon atoms such as methyl group and ethyl group; $R^1$ represents a divalent hydrocarbon residue with 2-3 carbon atoms such as ethylene group, propylene group, isopropylene group, and so on; $R^3$ represents a hydrogen atom or a methyl group; m represents an integer of 1-3, and n is 0 or 1.

The phenylene group combining an alkoxysilyl group with a (metha)acrylic group may be any of o-, m- and p-phenylene groups.

Typical examples of the compounds represented by the foregoing general formula are illustrated below.

-continued

-continued

-continued

These compounds can be synthesized be allowing compounds represented by the general formula, (wherein $R^1$ represents a monovalent hydrocarbon residue with 1-2 carbon atoms, $R^2$ represents a divalent hydrocarbon residue with 2-3 carbon atoms, X represents a halogen atom, m represents 1, 2 or 3, and n represents 0 or 1) to react with compounds represented by the general formula, (wherein $R^3$ represents a hydrogen atom or a methyl group, M represents an alkali or alkaline earth metal compound).

Also, the organosilicon compounds of this invention can be prepared using other processes: One process comprises allowing compounds of the general formula,

(Wherein $R^1$ is a monovalent hydrocarbon residue with 1-2 carbon atoms, and m is 1, 2 or 3) to react with compounds of the general formula, (wherein $R^3$ and $R^5$ each represents a hydrogen atom or a methyl group, n is 0 or 1, and p is 0 or 1) in the presence of a catalyst such as a platinum compound or so on, while another process comprises allowing compounds of the general formula, (wherein Y represents a halogen atom, and m represents 1, 2 or 3) to react with compounds of the general formula, (wherein $R^3$ and $R^5$ each represents a hydrogen atom or a methyl group, n represents 0 or 1, and p represents 0 or 1) in the presence of a catalyst such as a platinum compound or so on to produce the compounds represented by the general formula, ($R^2$ represents a divalent hydrocarbon residue with 2-3 carbon atoms, $R^3$ represents a hydrogen atom or a methyl group, m represents 1, 2 or 3, p represents 0 or 1, and Y represents a halogen atom), and allowing the thus produced compounds to react with compounds of the general formula, $R^1$OH (wherein $R^1$ represents a monovalent hydrocarbon residue with 1-2 carbon atoms).

The thus obtained organosilicon compounds relating to this invention are very useful as silane coupling agents, because not only they can be used as adhesives between various resins and all sorts of inorganic materials, but also they can be introduced into various kinds of resins through grafting or copolymerization reaction to make said resins moisture curable.

EXAMPLES

The present invention will now be illustrated in more detail by reference to the following examples. However, the invention should not be construed as being limited to these examples.

SYNTHESIS EXAMPLE 1

In a 1-liter separable flask equipped with a stirrer, a thermometer, a reflux condenser and a dropping funnel were placed 152.5 g (1.0 mole) of chloromethylstyrene represented by the formula, (a mixture constituted by 70% of meta-substituted product and 30% of para-substituted product), 150.0 g of toluene, 0.5 g of a 1-butanol solution of chloroplatinic acid having a platinum concentration of 2 wt %, and 0.5 g of BHT. Thereto, 135.5 g (1.0 mole) of trichlorosilane represented by the formula, H—SiCl$_3$, was added dropwise at 50° C. with stirring. In the dropwise addition, a temperature of the reaction system was controlled so as not to rise to 60° C. or higher. After the conclusion of the dropwise addition, the reaction system was further stirred for 2 hours at 70° C. Then, 270.0 g (4.5 moles) of urea was added to a 430 g portion of the thus obtained reaction mixture. Thereto, 192.0 g (6.0 moles) of methanol was added dropwise at 50° C. under the condition that a temperature inside the reaction system might not rise beyond 80° C.

After the conclusion of the dropwise addition, the stirring was further continued for 2 hours at 80° C., and then the reaction system was cooled. Upon cooling, the reaction system separated into two layers. The resulting upper layer was concentrated, and then distilled. Thus, 208.0 g of a colorless transparent liquid having a boiling point of 142° C. under pressure of 4 Torr. The thus obtained compound has turned out to have the following structural formula, from the results of spectroscopic analyses of its infrared absorption, nuclear magnetic resonance and mass spectra. The yield was 75.7%.

SYNTHESIS EXAMPLE 2

In the same manner as in Synthesis Example 1, except that 276.0 g (6.0 moles) of ethanol was used in place of methanol, 220.6 g of a colorless transparent liquid having a boiling point of 125° C. under pressure of 0.003 Torr was prepared. The thus obtained compound has turned out to have the following structural formula, from the results of spectroscopic analyses of its infrared absorption, nuclear magnetic resonance and mass spectra. The yield was 69.6%.

SYNTHESIS EXAMPLE 3

In the same manner as in Synthesis Example 1, except that 94.5 g (1.0 mole) of dimethylchlorosilane represented by the formula, was used in place of trichlorosilane, 181.2 g of a colorless transparent liquid having a boiling point of 129° C. under pressure of 4 Torr was obtained.

The thus obtained compound has turned out to have the following structural formula, from the results of spectroscopic analyses of its infrared absorption, nuclear magnetic resonance and mass spectra. The yield was 73.4%.

SYNTHESIS EXAMPLE 4

In the same manner as in Synthesis Example 1, except that 166.5 g (1.0 mole) of chloromethyl allylbenzene represented by the formula, was used in place of chloromethylstyrene of the formula, 215.6 g of a colorless transparent liquid having a boiling point of 110° C. under pressure of 0.01 Torr was obtained.

The thus obtained compound has turned out to have the following structural formula, from the results of spectroscopic analyses of its infrared absorption, nuclear magnetic resonance and mass spectra. The yield was 74.7%.

EXAMPLE 1

In a 1-liter separable flask equipped with a stirrer, a thermometer, a reflux condenser and a dropping funnel were placed 72.4 g (0.5 mole) of potassium methacrylate represented by the formula, 223 g of N,N-dimethylformamide, and 0.8 g of 2,6-di-t-butyl-4-methylphenol. Thereto, a 137.4 g portion (0.5 mole) of the material obtained in Synthesis Example 1, namely the compound represented by the formula, (mixture constituted by 70% of meta-substituted product and 30% of para-substituted product), was added dropwise at 100° C. After the conclusion of the dropwise addition, the stirring was further continued for 5 hours at 100° C., followed by a concentration procedure. Thus, 154 g of a dark brown transparent liquid was obtained.

A purity of this liquid checked by gas chromatography was 88.7% (made up to 62.5% of meta-substituted product and 26.2% of para-substituted product).

Further, this liquid was distilled to yield 62.7 g of a pale yellow transparent liquid having a boiling point of 145° C. under pressure of 0.001 Torr. A purity of the resulting liquid checked by gas chromatography was 95.4% (made up of 67.1% of meta-substituted product and 28.3% of para-substituted product).

The thus obtained compound was confirmed to have the following structural formula, from the results of spectroscopic analyses of its infrared absorption, nuclear magnetic resonance and mass spectra, and the result of elemental analysis.

The yield at the time of concentration was 83.7%, while that after the distillation was 36.8%.

<Results of Analyses>

Elemental Analysis:

| | Si | C | H |
|---|---|---|---|
| Anal. Calcd. | 8.66% | 59.23% | 7.46% |
| Found | 8.71% | 59.12% | 7.29% |

Analysis of Proton NMR Spectrum:
(See FIG. 1)

Figure 1:
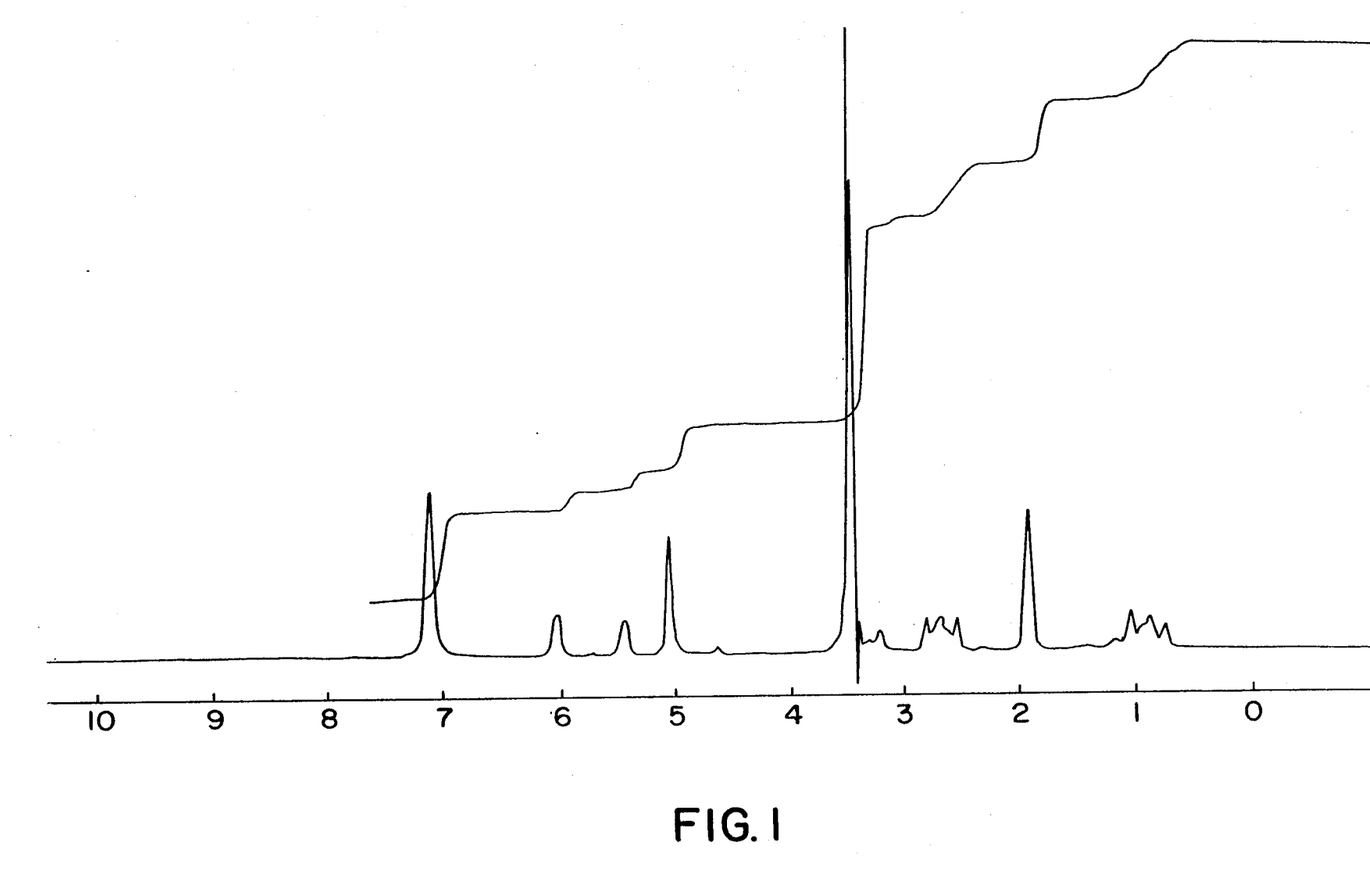
FIG. 1 is a proton NMR spectrum of the compound obtained in Example 1.

$\delta$ = 5.40~5.60 ppm(m, 1H): O CH$_3$
                                ‖  |
                                C—C=C$\underline{H}_2$ 6.00~6.20 ppm(m, 1H): O CH$_3$
                      ‖  |
                      C—C=C$\underline{H}_2$ 1.90 ppm(S, 3H):  O   O
                  ‖   ‖
                  C—C—C$\underline{H}_3$ 5.10 ppm(S, 2H): ⌬—C$\underline{H}_2$—O 7.00~7.40 ppm(m, 4H): ⌬—$\underline{H}$ 2.50~2.95 ppm(m, 2H): CH$_2$—C$\underline{H}_2$—⌬

0.75~1.25 ppm(m, 2H): Si—C$\underline{H}_2$—CH$_2$
3.50 ppm(S, 9H): C$\underline{H}_3$—O—Si Analysis of IR Spectrum:
(See FIG. 2)

Figure 2:
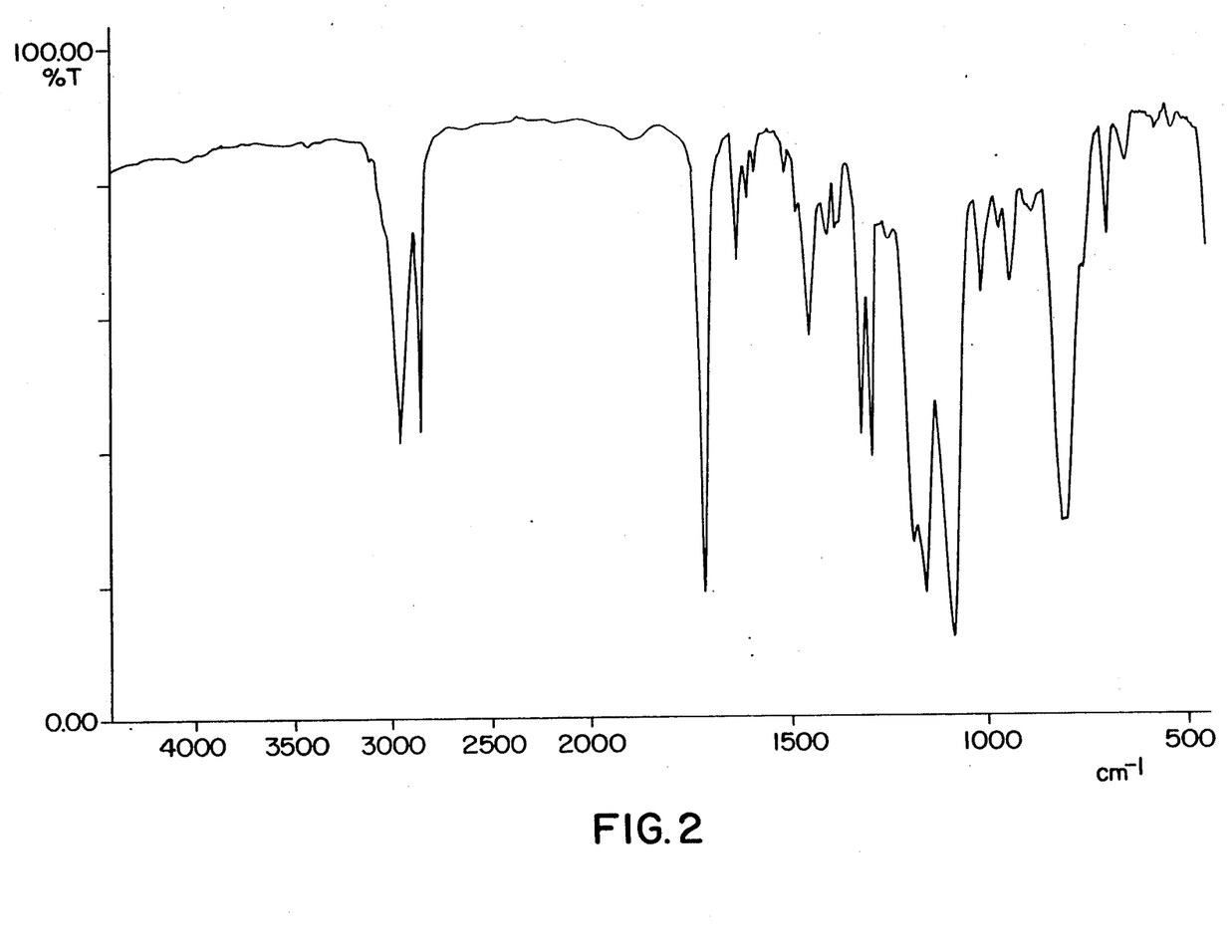
FIG. 2 is IR absorption spectrum of the compounds obtained in Examples 1.

1,087 cm$^{-1}$: Si—O—C 1,720 cm$^{-1}$: —C—O—
                  ‖
                  O 1,638 cm$^{-1}$: —C=C—
1,453 cm$^{-1}$: C—H
2,840 cm$^{-1}$: C—H
2,942 cm$^{-1}$: C—H

EXAMPLE 2

In the same manner as in Example 1, except that 72.4 g (0.5 mole) of potassium acrylate (KO(CO)CH=CH$_2$) was used in place of potassium methacrylate, the synthesis reaction was carried out to yield 130.0 g of a dark brown transparent liquid.

A purity of this liquid checked by gas chromatography was 92.5% (made up of 65.3% of meta-substituted product and 27.2% of para-substituted product).

Further, this liquid was distilled to yield 52.3 g of a pale yellow transparent liquid having a boiling point of 140° C. under pressure of 0.002 Torr. A purity of the resulting liquid checked by gas chromatography was 95.0% (made up of 67.4% of meta-substituted product and 27.6% of para-substituted product).

The thus obtained compound was confirmed to have the following structural formula, from the results of spectroscopic analyses of its infraredabsorption, nuclear magnetic resonance and mass spectra, and the result of elemental analysis.

The yield at the time of concentration was 77.6%, while that after the distillation was 32.1%.

<Results of Analyses>

Elemental Analysis:

| | Si | C | H |
|---|---|---|---|
| Anal. Calcd. | 9.05% | 58.04% | 7.14% |
| Found | 9.23% | 57.91% | 7.05% |

Analysis of Proton NMR Spectrum:

$\delta$ = 5.50~6.60 ppm(m, 3H): O
                                ‖
                                C—C$\underline{H}$=C$\underline{H}_2$ 5.10 ppm(S, 2H): ⌬—C$\underline{H}_2$—O 6.90~7.45 ppm(m, 4H): ⌬—$\underline{H}$ 2.45~2.95 ppm(m, 2H): CH$_2$—C$\underline{H}_2$—⌬

$\delta$ = 0.70~1.20 ppm(m, 2H): Si—C$\underline{H}_2$—CH$_2$
3.50 ppm(s, 9H): C$\underline{H}_3$—O—Si Anaylsis of IR Spectrum:
(See FIG. 2)

1,087 cm$^{-1}$: Si—O—C 1,720 cm$^{-1}$: —C—O—
                  ‖
                  O

1,637 cm$^{-1}$: —C=C—
1,454 cm$^{-1}$: C—H
2,841 cm$^{-1}$: C—H
2,942 cm$^{-1}$: C—H

EXAMPLE 3

In the same manner as in Example 1, except that 158.3 g (0.5 mole) of the compound, prepared in Synthesis Example 2, was used in place of the compound of the formula, used in Example 1, the synthesis reaction was carried out to yield 140.3 g of a dark brown transparent liquid.

A purity of this liquid checked by gas chromatography was 88.0% (made up of 64.3% of meta-substituted product and 23.7% of para-substituted product).

Further, this liquid was distilled to yield 21.0 g of a pale yellow transparent liquid having a boiling point of 169° C. under pressure of 0.001 Torr. A purity of the resulting liquid checked by gas chromatography was 94.5% (made up of 68.0% of meta-substituted product and 26.5% of para-substituted product).

The thus obtained compound was confirmed to have the following structural formula, from the results of spectroscopic analyses of its infrared absorption, nuclear magnetic resonance and mass spectra, and the result of elemental analysis.

The yield at the time of concentration was 67.5%, while that after the distillation was 10.9%.

EXAMPLE 4

In the same manner as in Example 1, expect that 121.3 g (0.5 mole) of the compound, prepared in Synthesis Example 3 was used in place of the compound, used in Example 1, the synthesis reaction was carried out to yield 136.2 g of a dark brown transparent liquid.

A purity of this liquid checked by gas chromatography was 87.9% (made up of 64.3% of meta-substituted product and 23.6% of para-substituted product).

Further, this liquid was distilled to yield 38.5 g of a pale yellow transparent liquid having a boiling point of 136° C. under pressure of 0.001 Torr. A purity of the resulting liquid checked by gas chromatography was 95.4% (made up of 68.0% of meta-substituted product and 27.4% of para-substituted product).

The thus obtained compound was confirmed to have the following structural formula, from the results of spectroscopic analyses of its infrared absorption, nuclear magnetic resonance and mass spectra, and the result of element analysis.

The yield at the time of concentration was 82.0%, while that after the distillation was 22.8%.

EXAMPLE 5

In the same manner as in Example 1, except that 144.3 g (0.5 mole) of the compound, prepared in Synthesis Example 4 was used in the place of the compound, used in Example 1, the synthesis reaction was carried out to yield 131.3 g of a dark brown transparent liquid.

A purity of this liquid checked by gas chromatography was 89.8%. Further, this liquid was distilled to yield 28.4 g of a pale yellow transparent liquid having a boiling point of 157° C. under pressure of 0.003 Torr. A purity of the resulting liquid checked by gas chromatography was 93.8%.

The thus obtained compound was confirmed to have the following structural formula, from the results of spectroscopic analyses of its infrared absorption, nuclear magnetic resonance and mass spectra, and the result of elemental analysis.

The yield at the time of cocentration was 69.8%, while that after the distillation was 15.8%.

What is claimed is:

1. Organosilicon compounds represented by the following general formula;

(wherein $R^1$ represents a monovalent hydrocarbon residue containing one or two carbon atoms, $R^2$ represents a divalent hydrocarbon residue containing two or three carbon atoms, $R^3$ represents a hydrogen atom or a methyl group, m represents an integer from 1 to 3, and n represents 0 or 1).

2. The organosilicon compounds of claim 1, wherein said $R^1$ is methyl group or ethyl group.

3. The organosilicon compounds of claim 1, wherein said $R^2$ is ethylene group, propylene group, or isopropylene group.

4. A method of synthesizing the organosilicon compounds of claim 1, which comprises allowing compounds represented by the following general formula, to react with compounds represented by the following general formula, (wherein $R^1$, $R^2$, $R^3$, m and n are the same as defined in claim 1, respectively; X represents a halogen atom; and M represents an alkali or alkaline earth metal compound).

5. A method of synthesizing the organosilicon compounds of claim 1, which comprises allowing compounds of the general formula, to react with compounds of the general formula, in the presence of a catalyst, wherein $R^1$, $R^3$, m and n are the same as defined in claim 1, respectively; $R^5$ is a hydrogen atom or a methyl group; and p represents 0 or 1.

6. The synthesis method of claim 5, wherein said catalyst is a platinum compound or metallic platinum.

7. A method of synthesizing the compounds of claim 1, which comprises allowing compounds of the general formula, (wherein Y represents a halogen atom, and m represents 1, 2 or 3) to react with compounds of the general formula, (wherein $R^3$ and $R^5$ each represents a hydrogen atom or a methyl group, n represents 0 or 1, and p represents 0 or 1) in the presence of a catalyst.

8. The synthesis method of claim 7, wherein said catalyst is a platinum compound or metallic platinum.

9. Moisture curable resins prepared by allowing the organosilicon compounds of claim 1 to undergo a copolymerization reaction with other compounds containing a polymerizing double bond, or to undergo a graft copolymerization reaction.

* * * * *